United States Patent [19]

Murray et al.

[11] 4,020,156

[45] Apr. 26, 1977

[54] CONTROLLED FRAGRANCE RELEASING CRYSTAL BEADS

[75] Inventors: Thomas E. Murray, Rockaway Township, N.J.; Vincent T. Bocchino, Port Chester, N.Y.

[73] Assignee: Norda Incorporated, New York, N.Y.

[22] Filed: Feb. 13, 1976

[21] Appl. No.: 658,038

[52] U.S. Cl. .................................. 424/76; 252/522; 424/16; 424/65

[51] Int. Cl.² ...................... A61K 7/46; A61K 7/50; A61L 9/01

[58] Field of Search .................. 424/76, 65, 14, 23; 252/522

[56] References Cited

UNITED STATES PATENTS 3,767,787  10/1973  Segal ..................................... 424/76

*Primary Examiner*—Dolph H. Torrence
*Attorney, Agent, or Firm*—Burns, Doane, Swecker & Mathis

[57] ABSTRACT

Fragrance releasing crystal beads are provided which gradually release a fragrance under anhydrous conditions and provide a rapid release of fragrance when wetted. The beads comprise a water-soluble particulate carrier, e.g. prilled urea, coated with a finely divided highly absorptive inorganic matrix containing the fragrance. The beads optionally include emollients and bacteriostats and the like and can be used for pleasingly perfumed sachets or as bath beads or as agents for the control of malodors in pet litter. The particulate beads may be conspicuously colored such that their color substantially disappears as they are dissolved, giving a visual indication of the need for replenishment.

8 Claims, No Drawings

CONTROLLED FRAGRANCE RELEASING CRYSTAL BEADS

BACKGROUND OF THE INVENTION

This invention relates to crystal beads having controlled fragrance releasing properties. More particularly this invention relates to crystal beads which contain an odor releasing material coated on the surface of a beaded or prilled water-soluble material such as urea. The products are useful as odorants or deodorants. They exhibit a slow continuous release of fragrance under anhydrous or dry conditions without the carrier being dissolved and exhibit a rapid release of fragrance when wetted.

For instance, if placed in the air intake of an air conditioner, the odor may be steadily released for two weeks or more under forced draft conditions. If wetted and the carrier is dissolved, the perfume released will be more intense and last several hours. The product of the present invention is not hygroscopic despite the high water solubility of the carrier used. Thus, exposure of the product to a steam atmosphere in a hood does not result in any appreciable softening, dissolution or apparent absorption of water, although these phenomena would occur with the carrier itself in the absence of the coating which is an essential feature of this invention.

Retarded vaporization compositions have been disclosed in the prior art which enable highly volatile fragrances and other odoriferous materials to be maintained in a relatively non-volatile state for extended periods of time and to be released when the composition is contacted with water. See, for instance, U.S. Pat. No. 3,767,787. Although these compositions are disclosed to have utility in a wide variety of usages including a vaporizer, a household deodorant, an insecticide and a dog repellant, they are not very efficient because the compositions are in the form of homogeneous, gelatine-like, non-aqueous colloidal systems from which the desired product is made by extrusion and curing. As the odoriferous material is uniformly distributed throughout, there is said to be no release of odor under ambient conditions, but only on contact with moisture when the composition changes to an aqueous system from which the volatile perfume is released.

U.S. Pat. No. 3,772,215 is another illustration of the state of the prior art. It also discloses compositions designed to provide a rapid release of fragrance upon contact with water. The compositions are water-soluble hydroxy-acrylate or methacrylate polymers in which fragrant materials are entrapped. In making this product, however, a relatively expensive water soluble polymer must be used which must be dissolved in a solvent such as methanol, the desired fragrance is added to the polymer solution, and the solution is cast as a thin film and ground to a powder after drying. This is a lengthy operation requiring several pieces of process equipment. By contrast, the product of the present invention can be made in a single vessel where the beads, as urea beads, and other components are heated to the proper temperature, mixed to insure proper dispersion and discharged in particulate form. The carrier is relatively inexpensive and available in a form that is ready for use.

It is an object of the invention to provide compositions which are economical to prepare and use and which enable fragrances to be slowly and continuously released over extended periods of time but which are also capable of rapidly releasing fragrances under controlled conditions.

It is another object of this invention to provide controlled fragrance releasing compositions which have a highly visible particulate appearance such that they indicate visually when the original charge is spent and replacement or replenishment is required.

These and other objects, as well as the scope, nature and utilization of the present invention will be apparent to those skilled in the art from the following description of the invention and from the appended claims.

SUMMARY OF THE INVENTION

According to the present invention compositions are provided which enable a fragrance to be released gradually over an extended period of time under anhydrous or ambient atmospheric conditions and which enable the fragrance to be rapidly released when wetted. They are formed by coating a water-soluble particulate carrier, such as a prilled urea, with a finely divided, highly absorptive inorganic matrix containing an absorbed fragrance. The finely divided inorganic matrix is adhered to the surface of the water-soluble carrier by means of a dextrin or similar gum.

In other embodiments of the invention the controlled fragrance releasing composition may include additional agents such as emollients or bacteriostats which are rapidly released when the compositons are contacted with water and which allow the compositions to be adapted for particular uses such as bath beads or disinfectants.

DESCRIPTION OF PREFERRED EMBODIMENTS

The controlled fragrance releasing compositions according to the present invention, which are sometimes referred to as crystal beads, are formed from a water-soluble bead or prill, e.g. urea, which serves as a carrier. The water-soluble bead is rendered non-hygroscopic because of the surface coating of an appropriate inorganic material such as tricalcium silicate, which protects the carrier bead from a humid atmosphere. It is desirable that the carrier be relatively hard and chemically inert to the fragrance oils and the gums or dextrins. The melting point should be above the processing temperature to maintain particle identity. Prilled urea fulfills all of the above criteria, in addition to being non-toxic. It is particularly useful because it disappears by solution as it is used and thus acts as its own indicator for replacement.

The water-soluble beads useful as the carrier for the fragrance releasing compositons of the invention have a particle size of from about 8 to 20 mesh, i.e., 1 mm to 3 mm maximum diameter, so as to provide a distinctly particulate appearance which is easy to discriminate visually.

The particle size distribution, while not critical, is preferably such as to permit the beads to be packed into suitable containers without creating too many fines and to be readily dispersed from simple containers with a perforated shaker top. Prilled urea having the indicated mesh size and particle size distribution suitable for use in the present invention is readily available in commerce.

The fragrance releasing compositions are formed from the water-soluble beads by coating the beads with a finely divided, highly adsorptive inorganic matrix in which the desired fragrance is absorbed. The inorganic matrix may be any natural or synthetic inorganic material capable of adsorbing the fragrance oils to be used in the invention. Non-limiting examples of inorganic materials useful as the matrix include synthetic calcium silicate, magnesium carbonate and fumed silicon dioxide such as Cab-O-Sil. The finely divided inorganic matrix should desirably have an average particle size of about 2 to about 5 microns.

The surface area of such materials may be in the range of from about 80 to about 400 sq. meters/gram. More particularly, for instance, it may be in the range of from about 95 to 175 sq. meters/gram in the case of a calcium silicate such as Microcel, about 160 sq. meters/gram in the case of Cab-O-Sil, or about 250 to 350 sq. meters/gram in the case of a micron-sized silicate such as Syloid.

Individual or mixed natural essential oils or suitable fragrant synthetic organic chemicals or mixtures of such natural and synthetic materials are useful as the fragrance of the compositions of the present invention. A wide variety of such materials is well known in the perfumer's art, as is their compounding to achieve special fragrant or malodor masking effects that may be desired. Useful fragrances include, for instance, floral oils such as rose oil, lilac, jasmine, wisteria, apple blossom, etc., or compounded bouquets such as spice, aldehydic, woody, oriental, mossy and the like.

The fragrance is adsorbed by the finely divided inorganic matrix by simple blending of the fragrance oil with the adsorptive solid employing conventional mixing or blending apparatus such as, for example, a ribbon blender. A vacuum chamber may be used to facilitate the impregnation of the inorganic matrix particles if desired. For most purposes the adsorption of 1 part of fragrance on from 1 to 3 parts of the adsorptive solid will provide compositions which enable satisfactory release of the fragrance under anhydrous conditions or when wetted.

The carrier is prepared to receive the fragrance by coating the carrier with a concentrated solution (about 60 to 70% by weight) of a dextrin in water. Dextrin is a water-soluble product formed by the hydrolysis of starches. Virtually any commercially available dextrin may be employed in this invention to coat the water-soluble carrier, provided that its concentration in the solution is within the proper range.

The coating of the carrier with the dextrin is carried out by simple mixing or blending of the carrier and the dextrin in a heated, agitated mixer or the like. The carrier beads are preferably pre-heated to at least about 50° C., e.g. 65° C., in a suitable mixing device such as a steam jacketed blending kettle and a suitable amount of dextrin solution based on the weight of the carrier beads is added to the kettle. Coating of the dextrin on the beads is effected by blending and heating the mixture at a temperature that is preferably at least 5° and more preferably at least 15° C below the melting point of the beads, e.g., in the case or urea beads, at from about 50° to 100° C., preferably 60° to 70° C. The temperature referred to is that of the particulate carrier and is measured by conventional means, i.e., a thermometer immersed in the moving mass. Blending under heat is desirable to accelerate evaporation of the water present, thereby tending to keep carrier dissolution low and the time required for blending short.

As the solution of the dextrin coats the carrier beads at the elevated temperature, the water is evaporated during the coating and blending, and very little of the water-soluble carrier is thus dissolved when the dextrin solution used has the proper concentration. That which is dissolved, is redeposited on the carrier beads as the coating operation progresses and water is evaporated from the mixture. More dilute dextrin solutions are undesirable because their higher water content causes excessive dissolution of the carrier particles, bringing about an undue loss in size of the carrier particles as well troublesome mushiness during processing.

Solubility considerations determine a concentration of 60–70% by weight for the aqueous dextrin solution. A minimum amount of water is desired at this point. Just enough for surface coating of the urea is desired.

The blending is continued for a time sufficient to coat the carrier beads uniformly. Generally 10 to 30 minutes of blending will do the job, and about 20 minutes has been found sufficient in the work more fully described below. Of course, the optimum blending time will vary somewhat depending on the concentration of dextrin, the relative amounts of dextrin and carrier, the temperature of the operation, and the size and type of the mixing equipment and the like, but it is easy to determine by empirical trial by any person skilled in the art. The amount of dextrin employed is that amount necessary to form a coating on the carrier beads of about 50 to about 150 microns, preferably about 75 to 120 microns thickness. Generally, about 4 to 8% by weight, preferably about 5 to 6%, based on the weight of the carrier, of the dextrin solution will be sufficient.

The dextrin solution may optionally contain a color to improve the aesthetic appeal or desired visibility of the final fragrance releasing composition. The coloring agent, which preferably is of the food approved variety to minimize risk in the event of accidental ingestion, may be added to the dextrin during the formation of the dextrin solution. Alternatively, the coloring agent may be added during the coating of the carrier particles with the dextrin solution.

The color, referred to herein alternatively as the coloring agent, may be a natural or synthetic colorant. It is difficult to specify a particular percentage of the color that should be added because of the tremendous range of tinctorial powers and because desired brightness and hue will vary. For most purposes, however, when a food approved color is used, its concentration in the range of from about 0.005% to about 0.05% by weight based on the weight of the dextrin solution is usually sufficient. When a colored dextrin solution is used, the thickness of the colored coating obtained therefrom in any given case can be closely estimated by visual inspection or optical measurement after splitting a bead open.

When the water-soluble carrier has been coated with the dextrin solution and most of the water has been evaporated, the carrier particles substantially retain or regain their discreteness but acquire a sticky surface. At this stage the carrier is coated with the perfumed finely divided adsorptive inorganic matrix by simple blending of the components using conventional mixing equpment, without being permitted to cool or agglomerate. Mixing or blending is carried out for a sufficient time to provide a uniform coating of the perfumed matrix on the carrier. Again, the mixing operation is conducted while heating, e.g. at a temperature between about 50° and 100° C. This is required because the dextrin-coated beads tend to stick to each other if they are allowed to cool to room temperature before the non-sticky perfumed inorganic matrix is dispersed on the surface of the sticky beads, thereby inhibiting agglomeration. After completion of the coating of the carrier beads with the fragrance containing inorganic matrix, the coated beads are cooled and discharged from the mixer as a free-flowing solid.

The relative amounts of perfumed or fragrance containing matrix and carrier will vary depending on the particle sizes of the matrix and carrier employed and the performance desired. Generally, however, the matrix will be employed in an amount of from 1 to 5%, preferably about 2.5% to about 3.5% by weight based on the weight of the carrier and calculated on the basis of the dried, i.e., not perfumed, matrix. A particular adsorbent matrix normally has a definite maximum capacity for the perfume to be held, and a certain maximum quantity of the perfume saturated matrix can be firmly adhered to the coated carrier beads without flaking, all of which can be readily determined by empirical tests which are then used as the basis for formulating a practical product. For satisfactory performance including resistance to atmospheric moisture, the product coating may consist essentially of about 0.2 to 2 parts of matrix per part by weight of dextrin, preferably about 0.5 to about 1.5 part by weight of matrix per part by weight of dextrin. The optimum ratio naturally depends to some extent on the geometry of the case and the desired performance, e.g., the thickness of the dextrin coating and its total external surface which the matrix particles are required to protect, the respective average particle sizes of the carrier beads and of the adsorbent matrix, the particular procedure by which the matrix is applied to or embedded in the dextrin layer, the relative ease with which one desired the product to respond to wetting, and so on.

Once the carrier has a sufficient amount of the inorganic perfumed matrix adhered on its surface, the matrix coating serves both as a perfume reservoir and as a sealant, slowing down the absorption of water vapor by the normally hygroscopics carrier beads. The water insoluble matrix entraps the fragrance while the dextrin coating adheres the perfumed matrix firmly to the water soluble carrier particles. The controlled fragrance releasing compositions of the invention gradually release their fragrance over extended periods of time, for example, they are capable of retaining a high level of fragrance for well over a year under substantially anhydrous and non-turbulent conditions, i.e., conditions of low air convection and in the absence of substantial amounts of water. The compositions provide a rapid release of fragrance, however, when wetted. As employed herein the term "wetted" is intended to mean when the compositions are contacted with water or other liquid, such as alcohol, which is a solvent for urea or other solid from which the carrier particles are constituted. On becoming wetted with such a liquid, the carrier composition dissolves and the resulting solution rapidly displaces the volatile perfume from the insoluble, inorganic matrix.

In other embodiments of the invention, the controlled fragrance releasing compositions of the invention may contain one or more additional agents which are released when the compositions are wetted and which enable the compositions to be adapted to particular usages.

In one embodiment, for instance, the compositions of the invention may contain an emollient such as isopropyl myristate or a lanoline alcohol or derivative, which makes the compositions particularly desirable as bath beads. Upon addition of the beads to water the fragrance is rapidly released along with the emollient. The emollient gives the skin a feeling of smoothness.

In another embodiment, a bactericide or bacteriostat which prevents or retards the growth of bacteria, is included in the compositions of the invention. The bactericide may be selected from a large number of known and proprietary compounds including, for example, quaternary ammonium salts, organic mercurial compounds, bisphenols, phenols, hexachlorophene and the like. Alkyl dimethyl benzyl ammonium chlorides such as those sold under the trademark "Hyamine" (Rohm and Haas Company) have been found to be particularly useful. Certain essential oils also have bactericidal properties and are, of course, useful in the invention.

A unique usage of the compositions of the invention is the control of malodors in pet litters. Sprinkling of the highly visible beads in the fresh litter will release the fragrance slowly. When the litter is wetted by animal excreta and mixed by the animal, an instantaneous surge of fragrance is released which covers the malodors. Use of the controlled fragrance releasing composition can extend the useful life of the litter especially if the composition contains a bactericide and/or bacteriostat. The bactericide and/or bacteriostat helps to control the odor of the litter. If the beads are colored, the color will disappear as the beads are dissolved and serve as a visible indicator for additional applications. The bactericide and/or bacteriostat-containing compositions may also be used as fragrant disinfectants, sanitizers and the like.

The amount of these additional agents included in the compositions of the invention may vary over a wide range depending on effectiveness and intended use. The emollient, however, may generally be employed in an amount of from 2 to 4% by weight based on the carrier whereas a bactericide and/or bacteriostat may generally be employed in an amount of from 0.1 to 0.5% weight percent based on the carrier.

The emollients, bactericides and the like may be added to the controlled fragrance releasing compositions in different ways depending on whether they are water soluble or oil soluble. For instance, water soluble materials can be conveniently included by dissolving them in the dextrin-dye solution before the latter is coated on the carrier beads. Oil soluble materials can be included by dissolving them in the perfume before it is adsorbed on the inorganic matrix.

The invention will be fully described by reference to the following working examples which illustrate certain preferred embodiments.

EXAMPLE I

Preparation of Crystal Beads for Sachets

A. In a first step, 17 lbs. of "Micro-Cel" synthetic calcium silicate, made by Johns Manville Co., were charged into a small ribbon blender (capacity 50 lbs.) The calcium silicate had a particle size in the range from 1 to 4 microns and a surface area in the range from 95 to 175 $mm^2/gram$. 20 lbs. of Rose Composition No. 7500 perfume were gradually added to the synthetic calcium silicate particles at room temperature over a period of ten minutes with mild agitation. Mixing was continued until the perfume oil was completely adsorbed and uniformly dispersed (about 15 minutes after completion of addition).

B. In a second step, 0.328 lb. of Certified color (0.082 lb. F.D.C. Blue No. 1 plus 0.246 lb. F.C.D. Yellow No. 5) was added to 8.20 lbs. of water in a steam agitated 5-gallon tank and the mixture was agitated until the color dissolved. 16.44 lbs. of dextrin ("K-Dex" No. 4484, a tapioca dextrin with a DE equivalence of 3.0, made by Stein Hall and Co., Inc.) was then slowly added to the dyed water over a period of about 5 minutes with rapid agitation and heated to 65° C. to dissolve the dextrin. The dextrin solution was held at 60°-65° C.

C. In a third step, 490 lbs. of prilled urea of an average particle size of 20 mesh were charged into an agitated steam jacketed Patterson ribbon mixer having a capacity of 100 gallons. The urea beads were slowly heated with agitation to 70° C. The dextrin solution was then added with agitation while maintaining the beads at a temperature between 65° and 70° C. and mixing was continued for about 10 to 15 minutes until the urea was uniformly coated.

D. Finally, in a fourth step, the perfumed calcium silicate was added to the slowly agitated coated urea in the Patterson mixer and mixed throughly for about 10 minutes until uniform with continued heating at about 60° to 70° C. The mass was then cooled by using cooling water on the jacket and discharged through a sifter to break up any lumps. The yield was approximately 500 lbs.

EXAMPLE II

Preparation of Crystal Beads for Pet Litter

A. To the small ribbon blender of Example I, there was charged 17 lbs. of the synthetic calcium silicate described in Example I, and 2.5 lbs. of "Hyamine 1662" germicide, a quaternary ammonium chloride sold by Rohm and Haas Company, and 20 lbs. of Baby Cologne Fragrance M 1660 perfume were slowly added with agitation to the calcium silicate and stirred for about 15 minutes until thoroughly adsorbed and blended.

This was then followed with steps (B), (C) and (D) as described in Example I to produce about 500 lbs. of a controlled fragrance releasing composition having a highly visible green particulate appearance and having particular utility in the control of odor and bacteria in pet litter.

EXAMPLE III

Preparation of Bath Beads

Following the procedures of Example II, 17 lbs. of "Syloid" silicon dioxide having a particle size of from 2 to 4 microns (sold by W. R. Grace and Company) were blended with 20 lbs. of Evergreen No. 617B perfume and 20 lbs. of isopropyl myristate to provide crystal beads which, when dissolved in bath water, provide a pleasing fragrance and a smooth emollient feeling.

It may be seen, therefore, that the controlled fragrance releasing compositions or crystal beads of this invention provide a stable, versatile form of fragrance having utility in a wide variety of applications. While the invention has been described exemplified by specific embodiments thereof, the foregoing specification should make it evident that many other modifications, variations and alternative can be made therein by persons skilled in the art without departing from the scope or spirit of the inventive concept disclosed. Accordingly, the invention is intended to embrace all such alternatives, modifications and variations as come within the spirit and scope of the appended claims.

What is claimed is:

1. A fragrant bead composition which comprises a multiplicity of prilled urea beads having an adherent surface coating consisting essentially of:
   a. finely divided particles of an adsorbent selected from the group consisting of calcium silicate, magnesium carbonate and silicon dioxide, said particles having a surface area of from about 80 to about 400 square meters per gram and containing a fragrance adsorbed therein, and
   b. dextrin, as a binder; said adsorbent being present in the composition in a ratio of from about 1 to 5 parts per 100 parts by weight of urea and being present in the coating in a ratio of about 0.2 to 2 parts per part by weight of dextrin, and the fragrance being present in a ratio of from 1 to 3 parts per part by weight of adsorbent.

2. A bead composition according to claim 1 wherein the coating also comprises an emollient.

3. A bead composition according to claim 1 wherein the adsorbent also contains a germicide.

4. A bead composition according to claim 1 wherein the coating also contains a food approved color.

5. A deodorant bead composition comprising a multiplicity of prilled urea beads having an adherent surface coating consisting essentially of:
   a. finely divided particles of an adsorbent selected from the group consisting of synthetic calcium silicate, magnesium carbonate and silicon dioxide, said particles having a surface area of from about 80 to about 400 square meters per gram and containing a germicide and a fragrance adsorbed therein, and
   b. dextrin as a binder;
   the adsorbent being present in the composition in a ratio of from about 1 to 5 parts per 100 parts by weight of urea and being present in the coating in a ratio of about 0.2 to 2 parts per part by weight of dextrin, the fragrance being present in a ratio of from 1 to 3 parts per part by weight of adsorbent, and the germicide being present in a ratio of from about 0.1 to 0.5% based on the weight of the urea.

6. A bead composition according to claim 5 wherein the adsorbent is a synthetic calcium silicate.

7. A bead composition according to claim 5 wherein the coating also contains a food approved color.

8. A deodorant pet litter bead composition comprising a multiplicity of prilled urea beads having an adherent surface coating consisting essentially of:
   a. finely divided adsorbent synthetic calcium silicate particles having a surface area of from about 80 to about 400 square meters per gram containing a germicide and a fragrance adsorbed therein,
   b. dextrin as a binder, and
   c. a food approved color;
   the silicate being present in the composition in a ratio of from about 1 to 5 parts per 100 parts by weight of urea and being present in the coating in a ratio of about 0.2 to 2 parts per part by weight of dextrin, the fragrance being present in a ratio of from 1 to 3 parts per part by weight of silicate, and the germicide being present in a ratio of from about 0.1 to 0.5% based on the weight of the urea.

* * * * *